United States Patent [19]
Rahman et al.

[11] Patent Number: 4,963,362
[45] Date of Patent: Oct. 16, 1990

[54] FREEZE-DRIED LIPOSOME MIXTURE CONTAINING CYCLOSPORIN

[75] Inventors: Yueh-Erh Rahman; Suresh Venkataram, both of Minneapolis, Minn.

[73] Assignee: Regents of the University of Minnesota, Minneapolis, Minn.

[21] Appl. No.: 217,089

[22] Filed: Jul. 7, 1988

Related U.S. Application Data

[63] Continuation of Ser. No. 83,773, Aug. 7, 1987, abandoned.

[51] Int. Cl.$^5$ .................... A61K 9/127; A61K 37/22; A61K 45/05
[52] U.S. Cl. ..................................... 424/450; 264/4.1; 264/4.3; 424/420; 428/402.2; 514/885
[58] Field of Search ................................ 264/4.3, 4.6; 428/402.2; 424/420, 450; 436/829; 514/885

[56] References Cited

U.S. PATENT DOCUMENTS

| | | | |
|---|---|---|---|
| 4,016,100 | 4/1977 | Suzuki et al. | 424/450 X |
| 4,117,118 | 9/1978 | Härri et al. | 514/11 |
| 4,229,360 | 10/1980 | Schneider et al. | 260/403 |
| 4,311,712 | 1/1982 | Evans et al. | 514/773 |
| 4,370,349 | 1/1983 | Evans et al. | 514/785 |
| 4,438,052 | 3/1984 | Weder et al. | 264/4.6 |
| 4,508,703 | 4/1985 | Redziniak et al. | 424/450 |
| 4,673,567 | 6/1987 | Jizomoto | 424/450 |

OTHER PUBLICATIONS

Beveridge et al., *Curr. Ther. Res.*, 30: 5–18, (1981).
Bowers, L. D. and Canafax, D. M., *Ther. Drug Monit.*, 6: 142–147, (1984).
Canafax, D. M., and Ascher, N. L., *Clin. Pharm.*, 2: 515–524, (1983).
Crommelin, D. J. A. and Van Bommel, E. M. G., *Pharm. Res.*, 1: 159–164, (1984).
Crowe et al., *Arch. Biochem. and Biophysics*, vol. 242: 240–247, (1985).
European Multicentre Trail, *Lancet*, 2: 57–60, (1982).
Forssen, E. A. and Tokes, Z. A., *Cancer Res.*, 43: 546–550, (1983).
Fransen, G. J., et al., *Int. J. Pharm.*, 33: 27–35, (1986).
Gordon et al., *Drug Dev. Ind. Pharm.*, 8: 465–473, (1982).
Gregoriadis, G. and Allison, Ed., "Liposomes in Biological Systems", John Wiley and Sons, New York, pp. 153–179, (1980).
Haynes et al., *Immunol. Letters*, 11: 343–349, (1985).
Hsieh et al., *Trans. Proc.*, 17: 1397–1400, (1985).
Merion et al., *N. Engl. J. Med.*, 310: 148–154, (1984).
Moyer et al., *Clin. Biochem.*, 19: 83–89, (1986).
Poznansky, M. and Juliano, R., *Pharmacol. Rev.*, 36: 277–366, (1984).
Rahman, A., et al., *Cancer Res.*, 42: 1817–1825, (1982).
Rosenthal et al., *Surg. Gynecol. Obstet.*, 157: 309–315, (1983).
Ryman, B. E. and Tyrrell; *Essays in Biochemistry*, 16: 49–98, P. N. Campbell and R. D. Marshall, Academic Press, London.
Strauss and Hauser, *Proc. Natl. Acad. Sci.*, U.S.A., vol. 83: 2422–2426, (Apr. 1986).
Strauss and Hauser, *Biochemica et Biophysica Acta*, 858: 169–180, (1986).
Stiller et al., *Science*, 223: 1362–1367, (1984).
The Merck Index, Tenth Edition, p. 2748.

*Primary Examiner*—Richard D. Lovering
*Attorney, Agent, or Firm*—Merchant, Gould, Smith, Edell, Welter & Schmidt

[57] ABSTRACT

The invention provides a freeze-dried potential liposome mixture having an amphipathic lipid and a cyclosporin or derivative thereof for use in possible liposome delivery of cyclosporin into cells. A method to produce the freeze-dried mixture is also disclosed. When reconstituted to yield liposomes in an aqueous medium, substantially all of the cyclosporin present in the freeze-dried mixture is encapsulated in the liposomes.

1 Claim, No Drawings

FREEZE-DRIED LIPOSOME MIXTURE CONTAINING CYCLOSPORIN

"This is a continuation, of application Ser. No. 83,773, filed Aug. 7, 1987", now abandoned.

TECHNICAL FIELD

This invention relates to freeze-dried liposome compositions and methods for preparing such compositions. More specifically, the present invention is directed to a freeze-dried potential liposome composition containing a cyclosporin. Redispersion of the freeze-dried composition yields liposomes incorporating all of the cyclosporin present in the composition prior to freeze-drying.

BACKGROUND

Cyclosporins are a group of biologically active fungal metabolites. The major components, cyclosporin A and C are non-polar cyclic oligopeptides with immunosuppressive, antifungal and antiphlogistic activity. Cyclosporin A is used frequently as a immunosuppressive agent in organ transplantation. Cyclosporin A is also under investigation for suppression of graft versus host disease in bone marrow transplants and studies have indicated its usefulness in treating diabetes mellitus (type 1). Stiller, et al. *Science,* 223: 1362-1367 (1984). A number of reports have proven that cyclosporin A is better than standard immunosuppressive drugs azathioprine and prednisone in maintaining the viability of heterotropic cadaveric renal, liver, lung, heart and pancreas transplants. European Multicentre Trial, *Lancet,* 2: 57-60 (1982).

While cyclosporin A is an extremely useful immunosuppressive agent potentially harmful side effects do exist. One harmful side effect which has been reported is nephrotoxicity. Merion et al., *New England Journal of Medicine* 310: 148-154 (1984); Rosenthal et al., *Surg. Gynecol. Obstet.* 157: 309-315 (1983). Delivery of appropriate dosages of cyclosporin A is also a problem. It has been reported that following oral administration, the bioavailability of cyclosporin A is very poor. Beveridge et al., *Curr. Ther. Res.,* 30: 5-18 (1981). Also, inter-subject variability is very high in the case of oral administration of cyclosporin A. Moyer et al., *Clin. Biochem.* 19: 83-89 (1986). In view of the drawbacks associated with oral administration of cyclosporin A, intravenous administration is the preferred route. However, the available intravenous formulation has been withdrawn from the market due to the toxicity of the carrier, cremophore. Development of an alternative intravenous dosage form of cyclosporin A is therefore needed.

It has been known that phospholipids under appropriate conditions can spontaneously reform, in the presence of water, into closed membrane systems. Electron microscopy reveals that these structures are made of a number of concentric bilayers of phospholipid molecules, and are called liposomes. The usefulness of liposomes as a membrane model system arises from the fact that, as the dry phospholipids undergo their sequence of molecular rearrangements, there is an opportunity for an unrestricted entry of hydrophilic solutes between the planes of hydrophilic head groups (aqueous compartments). Similarly, sequestration of hydrophobic solutes occurs within the hydrophobic bilayers. The result is the production of a delivery system that can contain varying amounts of the drug depending on the type of interaction between the solute and the phospholipid.

Many methods have been proposed for the preparation of liposomes, the first and most widely used being the film method. Briefly, lipids of the desired composition in a solution with an organic solvent are dried in the form of a thin film on the walls of a roundbottom flask. A hydrophobic drug can be included in the film at this stage. The dry film is hydrated by adding a suitable aqueous phase and gently swirling the flask. With a hydrophilic compound, an aqueous solution of it is used for hydration. The liposomes formed by this procedure generally have a number of concentric bilayers and are called multilamellar vesicles.

Liposomes have been evaluated as potential drug delivery systems to introduce biologically active material into cells. Poznansky and Juliano, *Pharmacol. Rev.,* 36:277-336 (1984); Ryman, B.E. and Tyrrell, D.A. 1980: Liposomes-Bags of Potential, Essays in Biochemistry 16: P.N. Campbell and R.D. Marshall, Academic Press, London pp. 49-98. Several routes of administration have been tried for the administration of liposomes, for example, intravenous, subcutaneous, intraperitoneal, and oral delivery. Gregoriadis and Allison, Ed. "Liposomes in Biological Systems", John Wiley & Sons, New York pp. 153-178 (1980) An important advantage with liposomal drug delivery is the change in tissue distribution and binding properties as compared to the free forms of the drug resulting in enhanced therapeutic index and decreased toxicity. Examples include decreased nephrotoxicity of cyclosporin A [(Hsieh et al., *Transplantation Proceedings,* Vol. XVII:1397-1400 (1985)], and reduced cardiotoxicity and nephrotoxicity of doxorubicin and cisplatin, respectively as compared to the free forms of the drugs. Rahman et al., *Cancer Res.,* 42:1817-1825 (1982); Forssen and Tokes, *Cancer Res.,* 43:546-550 (1983).

Historically liposomes have been studied as suspensions and only recently freeze-dried into a powder form to enable redispersion at the time of administration. Gorden et al., *Drug Dev. Ind. Pharm.,* 8:465-473 (1982); Crommelin and VanBommel, *Pharm. Res.* 1:159-164 (1984); Evans et al., U.S. Pat. Nos. 4,311,712 and 4,370,349. A systematic optimization of freeze-drying of liposomes has been done in the presence of various cryoprotectants using carboxyfluorescein as the marker Fransen et al., *Int. J. Pharm.* 33:27-35 (1986).

Liposomal instability has been a major concern for long-term storage. Several changes such as change in size distribution, drug content and sedimentation can occur upon storage for an extended period. Therefore, providing liposomes in a dry powder form that is readily redispersible is highly desirable. While freeze-drying has been employed to make dry powder liposome and drug mixtures, researchers have reported problems of leakage of the drug upon reconstitution. In some cases, liposomes have been stabilized using adjuvants such as sugars to maintain the integrity of liposomal membranes during freeze-drying. Strauss & Hauser, *Proc. Natl. Acad. Sci. USA,* Volume 83:2422-2426 (April 1986); Strauss et al., *Biochimica et Biophysica Acta* 858:169-180 (1986). In the Evans patents reconstituted preparations of liposomes having steroid encapsulated therein exhibited 28% loss of the amount of steroid present in the liposome preparation prior to freeze-drying. In another instance, the Evans patents report that liposomes formed after freeze-drying retained 28% of the Angiotensin II present in liposomes prior to freeze-drying. Accordingly, there is a need for a freeze-dried liposome composition containing cyclosporin which when reconstituted in an aqueous media yields liposomes which incorporate substantially all of the cyclosporin present in the composition prior to freeze-drying.

SUMMARY OF THE INVENTION

We have found that a freeze-dried potential liposome mixture containing cyclosporin can be prepared which when redispersed or reconstituted in an aqueous media yields liposomes incorporating substantially all of the cyclosporin present in the mixture prior to freeze-drying. The freeze-dried potential liposome mixture comprises an amphipathic lipid and cyclosporin preferably in a ratio from about 1-20:1 on a weight/weight basis. More preferably, the amphipathic lipid and cyclosporin are present in a ratio of from about 5-15:1. Most preferably, the ratio of amphipathic lipid to cyclosporin is from about 8-13:1. In a preferred embodiment the mixture is a freeze-dried powder, which upon redispersion in an aqueous medium yields liposomes having the same particle size distribution and encapsulation of cyclosporin as before freezedrying.

The present invention further relates to a process for producing a freeze-dried potential liposome mixture comprising: (a) mixing at least one liposomeforming amphipathic lipid with a cyclosporin or derivative thereof in an organic solvent to form a composition; (b) evaporating the solvent to form a film of the composition; (c) contacting the film with an aqueous buffer to form a hydrated liposome suspension; and (d) freeze-drying the hydrated suspension to form the freeze-dried potential mixture. The present invention can be used to provide an improved delivery system to introduce cyclosporin into cells.

DETAILED DESCRIPTION OF THE INVENTION

The freeze-dried potential liposome mixture of the invention is formed from an amphipathic lipid and a cyclosporin or derivative thereof. Any conventional freeze-drying procedure can be used to carry out the freeze-drying methods of the present invention and produce the potential liposome mixture. As defined herein, freeze-dried potential liposome mixture refers to freeze-dried mixtures obtainable according to this invention which, upon dispersion in a suitable aqueous medium provide the desired liposome preparations. Surprisingly, when the freeze-dried potential liposome mixture of the present invention is reconstituted or redispersed in a suitable aqueous medium such as distilled water, liposomes are formed which incorporate substantially all of the cyclosporin present in the mixture prior to freeze-drying.

Compounds containing both highly hydrophobic and highly polar groups are called amphipathic. In the present invention any amphipathic lipid which is known to be suitable for preparing liposomes by known methods can be used. A wide variety of lipids can be used in the present invention; however, non-immunogenic and biodegradable lipids are preferred. Examples of lipids that can be used include the phospholipids, for example the natural lecithins such as egg lecithin or soya bean lecithin or synthetic lecithins such as saturated synthetic lecithins such as dimyristoyl-phosphatidylcholine, dipalmitoyl-phosphatidylcholine or distearoylphosphatidylcholine or unsaturated synthetic lecithins, for example dioleyl-phosphatidylcholine or dilinoleylphosphatidylcholine. Either a single phospholipid or a mixture of phospholipids may be used. One preferred lipid is egg phosphatidylcholine.

According to the present invention the potential liposome mixture includes a cyclosporin or derivative thereof. Included among the cyclosporins are non-polar cyclic oligopeptides with immunosuppressive, antifungal and antiphlogistic activities such as cyclosporin A and cyclosporin C. Other oligopeptide metabolites which can be used in the present invention are cyclosporin B, D, E, F, G, H and I. The most preferred cyclosporin to be incorporated into or encapsulated by liposomes in the present invention is cyclosporin A which is a potent immunosuppressive agent used in organ transplantation.

In a preferred embodiment of the potential liposome mixture the amount of amphipathic lipid and cyclosporin are in a ratio of from about 1-20:1 (weight/weight), respectively. More preferably, the amount of amphipathic lipid and cyclosporin are in a ratio of from about 5-15:1 (weight/weight), respectively. Most preferably, the ratio of the amount of amphipathic lipid to the amount of cyclosporin is from about 8-13:1.

The freeze-dried potential liposome mixture can also include optional adjuvants which provide a negative or positive charge. Examples of substances which provide a negative charge include egg phosphatidic acid, dipalmitoyl-phosphatidic acid, dicetyl phosphate or beef brain ganglioside. Positive charge providing substances include stearylamine or stearylamine acetate. Other optional adjuvants include substances which affect the physical properties of the lipid bilayers in the liposomes in some desirable way, for example, rendering them more fluid or rigid as required, for example cholesterol. Although the reason is not yet fully understood, We have found that cyclosporin itself stabilizes liposomes, thereby eliminating the need for a stabilizing agent such as cholesterol in the present invention.

As indicated above, upon reconstituting the freeze-dried mixture in an aqueous media substantially all of the cyclosporin which was present in the mixture prior to freeze-drying is incorporated into the liposomes. In a preferred embodiment of the present invention from about 95% to 100% of cyclosporin encapsulated in liposomes prior to freeze-drying is incorporated into liposomes when the freeze-dried mixture is reconstituted. Most preferably, essentially all (e.g. at least 99.5%) of the cyclosporin which is present in liposomes formed prior to freeze-drying is incorporated in the liposomes formed when the freeze-dried mixture is reconstituted.

In the preferred embodiment, reconstituting the freeze-dried potential liposome mixture of the present invention yields liposomes having substantially the same particle size distribution as before freeze-drying ($p=0.02$). Specifically, the size of the cyclosporin containing liposome ranges from an average diameter of from about 1 to about 5 microns. Preferably, the average diameter of the liposomes ranges from about 2 to about 4 microns.

Surprisingly, the freeze-dried potential liposome mixture according to the present invention can be stored for extended periods of time without loss of stability (i.e. loss of encapsulated cyclosporin). Freezedried liposome mixtures prepared in accordance with the methods of Example 1 herein can be stored for at least 120 days and retain at least 90% of the cyclosporin encapsulated in liposomes prior to freeze-drying. Further, while not necessary to the present invention, the freeze-dried potential liposome mixture can include various saccharides to impart cryoprotective effects and enhance long-term stability of the liposomes. Examples of useful saccharides include sucrose, trehalose, and glucose.

The freeze-dried potential liposome composition described above can be readily prepared by mixing at least one liposome-forming amphipathic lipid and a cyclosporin or derivative thereof with an organic solvent in a suitable reaction vessel. A wide variety of solvents can be used. However, organic solvents are preferred; especially solvents capable of evaporating easily. Examples of useful organic solvents include alcohols such as ethanol, methanol; ethers such as petroleum ether, diethyl ether; and chloroform and hexane. Preferably, organic solvents such as anhydrous methanol or chloroform are used.

While the amounts of the amphipathic lipid and cyclosporin can be varied greatly by one of skill in the art, preferably the amounts of amphipathic lipid and cyclosporin mixed together with the solvent are in a ratio of from about 1-20:1 (weight/weight), respectively. More preferably, the amounts of amphipathic lipid and cyclosporin are in a ratio of from about 5-15:1 (weight/weight) respectively. Most preferably, the amphipathic lipid and cyclosporin initially mixed together are in a ratio of from about 8-13:1 (weight/weight), respectively.

After mixing the amphipathic lipid, cyclosporin and solvent to form a liquid composition, the solvent is evaporated to form a film of the composition on the reaction vessel. The deposited film is then contacted with an aqueous medium to form a liposome suspension. Specifically, the film is hydrated in an aqueous medium such as distilled water, isotonic saline, or a sterile or non-sterile buffer solution and subjected to agitation. The liposomes can be formed in the aqueous medium by a number of methods known in the art, including sonication, swirling, stirring, shaking and vortexing. In the preferred embodiment liposomes are formed by hydrating the film in a phosphate buffered saline solution with the aid of swirling or vortexing. Formation of the freeze-dried potential liposome mixture is accomplished by freezing the liposome suspension formed above followed by lyophilizing the liposome suspension in a lyophilizer, such as the Virtis (freezemobile 12) until a dry powder is produced. Conventional freezing and lyophilization procedures can be used. Preferred freezing techniques include ice baths containing dry ice and acetone, or dry ice and isopropanol, or other freezing mixtures. While the lyophilization conditions can be varied by one of skill in the art, lyophilization is preferably conducted at a temperature from about between $-30°$ C. and $-70°$ C. and 50 to 100 millitorr of vacuum.

To reconstitute the freeze-dried potential liposome mixture any number of aqueous media can be used including distilled water, isotonic saline or a sterile or non-sterile buffer solution. Distilled water is preferred. However, if desired, certain electrolytes such as sodium, potassium or calcium can also be added. Numerous methods can be used to reconstitute the freezedried liposome mixture including swirling, stirring, shaking and vortexing. Preferably gentle shaking of the freeze-dried liposome mixture and aqueous medium is used to form the liposome preparation.

The invention is further illustrated by the following specific examples, which should not be used in limiting the scope of the invention. In the examples, which contain a best mode, all parts are in parts by weight unless otherwise specifically indicated.

EXAMPLE 1

Egg Phosphatidylcholine (EPC; 50 mg), Cholesterol (CHOL; 8.05 mg) and Cyclosporin A (CyA; 5.0 mg) were dissolved in chloroform (20 mL) in a 100 mL round-bottom flask. The solvent was evaporated in a rotary evaporator under vacuum at 40° C. The film was hydrated using phosphate buffered saline (PBS) (5 mL) with the aid of swirling and vortexing for approximately 15 minutes. The liposomes formed were analyzed for size homogeneity using a laser particle sizer. The average diameter of 93.2% of the population was found to be $2.37 \pm .21$ $\mu$. Aliquots of liposomal suspension were diluted 3-fold with PBS, and filtered through 0.2 $\mu$ Gelman ® membrane filter to separate unentrapped drug from the liposomes. HPLC analysis of the filtrate showed that it did not contain any CyA, meaning, 100% of the drug was associated with the liposomes. Analysis of the liposomal suspension accounted for 96% of the CyA input.

The liposomes were frozen at $-55°$ C. in a round-bottom flask in a bath containing a mixture of dry ice and isopropanol. The samples were lyophilized in a lyophilizer for 12 hours at $-55°$ C. and 50 millitorr and produced a dry light yellow powder. The dry powder was stored in the freezer until required for reconstitution. Typically, the powder was stored for 12 hours, however, results showed no difference even after 120,days of storage. Reconstitution was carried out using 4.5 mL of distilled water by gently shaking the flask for approximately 5 minutes. The reformed liposomes were treated as described above (laser particle sizer; filtration and HPLC analysis) to quantify CyA in the liposomes. The % incorporation of CyA was found to be unchanged after lyophilization as compared to before meaning 100% of the drug was associated with the liposomes. Particle size analysis showed that the mean diameter of 94.8% of the population was $3.42 \pm 0.2$ $\mu$. This was not significantly different from the size distribution before lyophilization (p=0.02).

EXAMPLE 2

EPC (48.3 mg), phosphatidic acid (PA; 6.0 mg) and CyA (4.98 mg) were dissolved in chloroform (20 mL) in a 100 mL round-bottom flask. The solvent was evaporated in a rotary evaporator under vacuum at 40° C. The dry film was hydrated using PBS (5 mL) with the aid of swirling, and vortexing for approximately 15 minutes. The liposomes formed were analyzed for size homogeneity using a laser particle sizer. The liposomes were found to have an average diameter of $2.8 \pm 0.2$ $\mu$. Aliquots of liposomal suspension were diluted 3-fold with PBS and filtered through 0.2 $\mu$ Gelman ® membrane filter to separate the unentrapped drug from the liposomes. HPLC analysis of the filtrate showed that it did not contain any CyA, meaning, 100% of the drug was associated with the liposomes. Analysis of the liposomal suspension accounted for 92% of the CyA input.

The liposomes were frozen at $-55°$ C. in a round-bottom flask in a bath containing a mixture of dry ice and isopropanol. The samples were lyophilized for 12 hours in the manner described in Example 1 and produced a dry light yellow powder. The dry powder was stored for at least 12 hours in the freezer until required for reconstitution. Reconstitution was carried out using 4.5 mL of distilled water by gently shaking the flask for approximately 5 minutes. The reformed liposomes were treated as described above (laser particle sizer; filtration and HPLC analysis) to quantify CyA in the filtrate. The % incorporation of CyA was found to be the same as compared to before lyophilization meaning 100% of the drug was associated with the liposomes. The mean diameter of 93% of the population was $2.98 \pm 0.2$ $\mu$. This was not statistically different from the size before lyophilization.

EXAMPLE 3

EPC (50 mg) of CyA (5 mg) were dissolved in chloroform (20 mL) in a 100 mL round-bottom flask. The solvent was evaporated in a rotary evaporator under vacuum at 40° C. The dry film was hydrated using PBS (5 mL) with the aid of swirling and vortexing for approximately 15 minutes. The liposomes formed were analyzed for size homogeneity using a laser particle sizer. The liposomes were found to have an average diameter of $2.6 \pm 0.3$ $\mu$. Aliquots of liposomal suspension were diluted 3-fold with PBS and filtered through 0.2 $\mu$ Gelman ® membrane filter to separate unentrapped drug from the liposomes. HPLC analysis of the filtrate showed that it did not contain any CyA, meaning 100% of the drug was associated with the liposomes. Analysis of the liposomal suspension accounted for 93% of the CyA input.

The liposomes were frozen at $-55°$ C. in a bath containing a mixture of dry ice and isopropanol. The samples were lyophilized for 12 hours in the manner described in Example 1 to produce a dry light yellow powder. The dry powder was stored in the freezer at least 12 hours until required for reconstitution. Reconstitution was carried out using 4.5 mL of distilled water by gently shaking the flask for approximately 5 minutes. The reformed liposomes were treated as described above (laser particle sizer; filtration and HPLC analysis) to quantify CyA in the filtrate. The % incorporation of CyA was found to be the same as compared to before lyophilization meaning 100% of the drug was associated with the liposomes. The mean diameter of 95% of the population was found to be $3.1 \pm 0.3$ $\mu$ which was not statistically different from the size before lyophilization.

EXAMPLE 4

Lyophilization of the components before the formation of liposomes.

EPC (50 mg) and CyA (5 mg) were dissolved in chloroform (20 mL) in a 100 mL round-bottom flask. The solvent was evaporated in a rotary evaporator under vacuum at 40° C. The dry film was lyophilized for 12 hours. Reconstitution was carried out using 5 mL of PBS by gently shaking the flask. The liposomes were diluted 3-fold with PBS and filtered through 0.2 $\mu$ Gelman ® membrane filter to separate unentrapped drug from the liposomes. HPLC analysis of the filtrate showed it did not contain any CyA meaning 100% of the drug was associated with the liposomes. The liposomes were found to have an average diameter of 1.6 $\mu$. Analysis of the liposomal suspension accounted for 94% of the CyA input.

What is claimed is:

1. A freeze-dried liposome mixture comprising an amphipathic lipid and a cyclosporin, said mixture being essentially free of saccharide and being storable for at least 120 days and wherein at least 90% of said cyclosporin in said mixture is encapsulated in liposomes of substantially uniform particle size distribution when an aqueous liposome preparation is prepared subsequent to said storage.

* * * * *